United States Patent
Kita-Tokarczyk et al.

(10) Patent No.: US 11,439,576 B2
(45) Date of Patent: *Sep. 13, 2022

(54) COSMETIC COMPOSITIONS COMPRISING FATTY ACID ESTERS OF OXALKYLATED ALKYLALKYLENE DIAMINES AND/OR THEIR SALTS FOR HAIR REPAIR TREATMENTS

(71) Applicant: Clariant International Ltd., Muttenz (CH)

(72) Inventors: Katarzyna Kita-Tokarczyk, Bad Soden (DE); Anton Kratz, Frankfurt am Main (DE); Nadine Zoumpoulakis, Frankfurt am Main (DE)

(73) Assignee: CLARIANT INTERNATIONAL LTD, Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/975,657

(22) PCT Filed: Mar. 11, 2019

(86) PCT No.: PCT/EP2019/056062
§ 371 (c)(1),
(2) Date: Aug. 25, 2020

(87) PCT Pub. No.: WO2019/175124
PCT Pub. Date: Sep. 19, 2019

(65) Prior Publication Data
US 2020/0405607 A1    Dec. 31, 2020

(30) Foreign Application Priority Data
Mar. 12, 2018 (EP) .................... 18161165

(51) Int. Cl.
*A61Q 5/00* (2006.01)
*A61Q 5/12* (2006.01)
*A61K 8/45* (2006.01)
*A61K 8/34* (2006.01)
*A61K 8/41* (2006.01)

(52) U.S. Cl.
CPC ............ *A61K 8/45* (2013.01); *A61K 8/342* (2013.01); *A61K 8/416* (2013.01); *A61Q 5/12* (2013.01); *A61K 2800/48* (2013.01)

(58) Field of Classification Search
None
See application file for complete search history.

(56) References Cited

U.S. PATENT DOCUMENTS

| 4,185,087 | A | 1/1980 | Morlino | |
| 10,993,898 | B2 * | 5/2021 | Leinweber | A61K 8/342 |
| 2012/0204894 | A1 * | 8/2012 | Odoms | A61K 8/678 |
| | | | | 132/202 |
| 2016/0317410 | A1 * | 11/2016 | Leinweber | A61K 8/342 |

FOREIGN PATENT DOCUMENTS

WO    2015110269    7/2015

OTHER PUBLICATIONS

Machine Translation of WO2018036105, Mar. 1, 2018, 30 pages.
International Search Report for PCT/EP2019/056062, dated Apr. 16, 2019, 2 pages.

* cited by examiner

*Primary Examiner* — Jyothsna A Venkat
(74) *Attorney, Agent, or Firm* — Tod A. Waldrop

(57) ABSTRACT

The use of a component for strengthening keratinous fibres or protecting keratinous fibres from damage, wherein the component is an ester of a certain oxalkylated alkylalkylene diamine and/or a quaternized salt thereof.

12 Claims, No Drawings

COSMETIC COMPOSITIONS COMPRISING FATTY ACID ESTERS OF OXALKYLATED ALKYLALKYLENE DIAMINES AND/OR THEIR SALTS FOR HAIR REPAIR TREATMENTS

FIELD OF THE INVENTION

The present invention relates to the use of a component for strengthening keratinous fibres or protecting keratinous fibres from damage.

BACKGROUND OF THE INVENTION

Human hair is subjected to much stress every day, including mechanical (combing, brushing, rubbing), chemical (hair washing, coloration), thermal (blow drying and straightening), as well as everyday elements (UV light, wind). As a result, hair fibres become weaker and break easily. Weak and damaged hair demonstrates itself as frizzy and difficult to align/style because of the uneven surface of the cuticle layer. Additionally, hair becomes weakened in the cortex, which leads to easier breakage.

The cosmetic industry has introduced consumer products which claim to repair or protect or strengthen the hair or prevent breakage. To support those advertising claims, typical conditioning ingredients are used, such as quaternary ammonium compounds, silicones, oils, hydrolyzed proteins, etc.

General hair treatment compositions for hair care are known, however there is still a need of compositions designed for hair care, which are based on easily available components. These compositions can improve combing and gloss properties for several hair types.

In WO2015110269A1 (application number PCT/EP2015/000136), which published on 30 Jul. 2015, a new class of ingredient for hair conditioning was described: fatty acid esters of oxalkylated alkylalkylene diamines and/or their salts. Materials from this group have superior properties for conditioning of hair regarding detangling.

Nevertheless there is a need for products and regimes suitable for advanced hair care such as hair repair and strengthening.

SUMMARY OF THE INVENTION

In a first aspect, the present invention relates to the use of a component for strengthening keratinous fibres or protecting keratinous fibres from damage, wherein the component is an ester of an oxalkylated alkylalkylene diamine of formula (I)

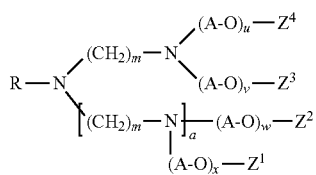

(I)

wherein
R denotes $C_8$-$C_{24}$-alkyl or $C_8$-$C_{24}$-alkenyl
A denotes a group —$C_2H_4$— or —$C_3H_6$—, in particular a group —$C_2H_4$—
$Z^1$ denotes a group —C(O)—R', wherein R' denotes $C_5$-$C_{35}$-alkyl or $C_5$-$C_{35}$-alkenyl, in particular $C_8$-$C_{24}$-alkyl or $C_8$-$C_{24}$-alkenyl,
$Z^2$ denotes a group —C(O)—R", wherein R" denotes $C_5$-$C_{35}$-alkyl or $C_5$-$C_{35}$-alkenyl, in particular $C_8$-$C_{24}$-alkyl or $C_8$-$C_{24}$-alkenyl,
$Z^3$ denotes a group —C(O)—R'", wherein R'" denotes $C_5$-$C_{35}$-alkyl or $C_5$-$C_{35}$-alkenyl, in particular $C_8$-$C_{24}$-alkyl or $C_8$-$C_{24}$-alkenyl,
$Z^4$ denotes a group —C(O)—R"", wherein R"" denotes $C_5$-$C_{35}$-alkyl or $C_5$-$C_{35}$-alkenyl, in particular $C_8$-$C_{24}$-alkyl or $C_8$-$C_{24}$-alkenyl,
a denotes 0 or 1, in particular 0
m denotes 2 or 3, in particular 3
u, v, w and x are each independently numbers from 1 to 9, in particular 2 to 9
where the sum of u, v and w being from 3 to 30, if a=0, and
where the sum of u, v, w and x being from 4 to 35, if a=1, and/or a quaternized salt thereof.

DETAILED DESCRIPTION OF THE INVENTION

Definitions and General

In this document, including in all embodiments of all aspects of the present invention, the following definitions apply unless specifically stated otherwise. All percentages are by weight (w/w) of the total composition. All ratios are weight ratios. "wt %" means percentage by weight. References to 'parts' e.g. a mixture of 1 part X and 3 parts Y, is a ratio by weight. "QS" or "QSP" means sufficient quantity for 100% or for 100 g.+/− indicates the standard deviation. All ranges are inclusive and combinable. The number of significant digits conveys neither a limitation on the indicated amounts nor on the accuracy of the measurements. All numerical amounts are understood to be modified by the word "about". All measurements are understood to be made at 23° C. and at ambient conditions, where "ambient conditions" means at 1 atmosphere (atm) of pressure and at 50% relative humidity. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International. Herein "min" means "minute" or "minutes". Herein "mol" means mole. Herein "g" following a number means "gram" or "grams". "Ex." means "example". All amounts as they pertain to listed ingredients are based on the active level ('solids') and do not include carriers or by-products that may be included in commercially available materials. Herein, "comprising" means that other steps and other ingredients can be in addition. "Comprising" encompasses the terms "consisting of" and "consisting essentially of". The compositions, formulations, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "In at least one embodiment" means that one or more embodiments, optionally all embodiments or a large subset of embodiments, of the present invention has/have the subsequently described feature. Where amount ranges are given, these are to be understood as being the total amount of said ingredient in the composition, or where more than one species fall within the scope of the ingredient definition, the total amount of all ingredients fitting that definition, in the composition. For example, if the composition comprises from 1% to 5% fatty alcohol, then a composition comprising 2% stearyl alcohol and 1% cetyl alcohol and no other fatty alcohol, would fall within this scope.

"Independently selected from," means that the referenced groups can be the same, different, or a mixture thereof, unless the context clearly indicates otherwise. Thus, under this definition, the phrase "X1, X2, and X3 are independently selected from noble gases" would include the scenario where X1, X2, and X3 are all the same, where X1, X2, and X3 are all different, and where X1 and X2 are the same but X3 is different.

"Molecular weight" or "M.Wt." or "MW" and grammatical equivalents mean the number average molecular weight.

"Viscosity" is measured at 25° C. using a HAAKE Rotation Viscometer VT 550 with cooling/heating vessel and sensor systems according to DIN 53019 at a shear rate of 12.9 s$^{-1}$.

"Water-soluble" refers to any material that is sufficiently soluble in water to form a clear solution to the naked eye at a concentration of 0.1% by weight of the material in water at 25° C. The term "water-insoluble" refers to any material that is not "water-soluble".

"Dry" or "substantially dry" means comprising less than 5%, less than 3% or, less than 2%, less than 1%, or about 0% of any compound or composition being in liquid form when measured at 25° C. at ambient conditions. Such compounds or compositions being in liquid form include water, oils, organic solvents and other wetting agents. "Anhydrous" means that the composition comprises less than 5%, less than 3% or, less than 2%, less than 1%, or about 0% water by total weight of the composition.

"Substantially free from" or "substantially free of" means less than 1%, or less than 0.8%, or less than 0.5%, or less than 0.3%, or about 0%, by total weight of the composition or formulation.

"Hair" means mammalian keratin fibres including scalp hair, facial hair and body hair. It includes such hair still being attached to a living subject and also hair that has been removed therefrom such as hair swatches and hair on a doll/mannequin. In at least one embodiment, "hair" means human hair. "Hair shaft" or "hair fibre" means an individual hair strand and may be used interchangeably with the term "hair."

"Proximal to the scalp" means that portion of an extended, or substantially straightened, hair shaft that is closer in distance to the scalp than to the end of the hair. Thus, about 50% of the hair fibre length would be considered proximal to the scalp, and about 50% of the hair fibre would be distal to the scalp. "z cm proximal to the scalp" means a distance "z" along the hair, with one endpoint being on or directly adjacent to the scalp, and the second endpoint being measured "z" centimetres along the length of the extended or substantially straightened hair.

"Chemically modify" or grammatical equivalents thereof, means that a chemical moiety such as monomer and/or crosslinker and/or polymer, stably affixes to a second chemical moiety, for example, a keratin protein, another component of hair, and/or another monomer or crosslinker or polymer. Normally, "chemically modify" means stably affix via a covalent bond, unless otherwise stated.

"Cosmetically acceptable" means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives" includes but is not limited to, amide, ether, ester, amino, carboxyl, acetyl, acid, salt and/or alcohol derivatives of a given compound. In at least one embodiment, "derivatives thereof" means the amide, ether, ester, amino, carboxyl, acetyl, acid, salt and alcohol derivatives.

"Monomer" means a discrete, non-polymerised chemical moiety capable of undergoing polymerisation in the presence of an initiator or any suitable reaction that creates a macromolecule e.g. such as polycondensation, polyaddition, anionic or cationic polymerization. "Unit" means a monomer that has already been polymerised i.e. is part of a polymer.

"Polymer" means a chemical formed from the polymerisation of two or more monomers. The term "polymer" shall include all materials made by the polymerisation of monomers as well as natural polymers. Polymers made from only one type of monomer are called homopolymers. Herein, a polymer comprises at least two monomers. Polymers made from two or more different types of monomers are called copolymers. The distribution of the different monomers can be random, alternating or block-wise (i.e. block copolymer). The term "polymer" used herein includes any type of polymer including homopolymers and copolymers.

"Kit" means a package comprising a plurality of components. "Kit" may be referred to as "kit-of-parts". An example of a kit is, for example, a first composition and a separately packaged second composition and optionally application instructions.

EXPLANATION OF AND BENEFITS PROVIDED BY THE INVENTION

Surprisingly, it has now been found that esters of certain oxalkylated alkylalkylene diamines or salts of such esters have a superior effect on hair strengthening and prevention of hair breakage.

The details of the invention and its aspects are provided hereinafter.

First Aspect

The first aspect relates to the use of a component for strengthening keratinous fibres or protecting keratinous fibres from damage, wherein the component is an ester of an oxalkylated alkylalkylene diamine of formula (I)

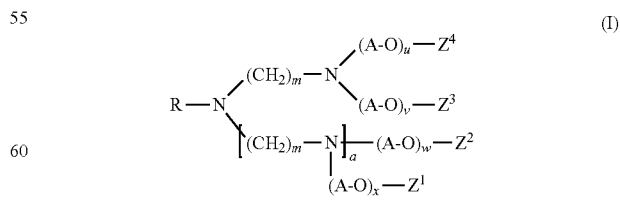

wherein
R denotes $C_8$-$C_{24}$-alkyl or $C_8$-$C_{24}$-alkenyl
A denotes a group —$C_2H_4$— or —$C_3H_6$—, in particular a group —$C_2H_4$—

$Z^1$ denotes a group —C(O)—R', wherein R' denotes $C_5$-$C_{35}$-alkyl or $C_5$-$C_{35}$-alkenyl, in particular $C_8$-$C_{24}$-alkyl or $C_8$-$C_{24}$-alkenyl, $Z^2$ denotes a group —C(O)—R", wherein R" denotes $C_5$-$C_{35}$-alkyl or $C_5$-$C_{35}$-alkenyl, in particular $C_8$-$C_{24}$-alkyl or $C_8$-$C_{24}$-alkenyl, $Z^3$ denotes a group —C(O)—R''', wherein R''' denotes $C_5$-$C_{35}$-alkyl or $C_5$-$C_{35}$-alkenyl, in particular $C_8$-$C_{24}$-alkyl or $C_8$-$C_{24}$-alkenyl, $Z^4$ denotes a group —C(O)—R'''', wherein R'''' denotes $C_5$-$C_{35}$-alkyl or $C_5$-$C_{35}$-alkenyl, in particular $C_8$-$C_{24}$-alkyl or $C_8$-$C_{24}$-alkenyl, a denotes 0 or 1, in particular 0
m denotes 2 or 3, in particular 3
u, v, w and x are each independently numbers from 1 to 9, in particular 2 to 9
where the sum of u, v and w being from 3 to 30, if a=0, and
where the sum of u, v, w and x being from 4 to 35, if a=1,
and/or a quaternized salt thereof.

In at least one embodiment, the component is an ester of an oxalkylated alkylalkylene diamine of formula (I), wherein
R denotes $C_8$-$C_{24}$-alkyl or $C_8$-$C_{24}$-alkenyl
A denotes a group —$C_2H_4$—
$Z^1$ denotes —C(O)—R', wherein R' denotes $C_8$-$C_{18}$-alkyl or $C_8$-$C_{18}$-alkenyl
$Z^2$ denotes —C(O)—R", wherein R" denotes $C_8$-$C_{18}$-alkyl or $C_8$-$C_{18}$-alkenyl
$Z^3$ denotes —C(O)—R''', wherein R''' denotes $C_8$-$C_{18}$-alkyl or $C_8$-$C_{18}$-alkenyl
$Z^4$ denotes —C(O)—R'''', wherein R'''' denotes $C_8$-$C_{18}$-alkyl or $C_8$-$C_{18}$-alkenyl
a denotes 0
m denotes 2 or 3, in particular 3
u, v and w are each independently numbers from 3 to 9
where the sum of u, v and w being from 6 to 30,
and/or a quaternized salt thereof, where the salt is formed by quaternizing one or two of the nitrogen atoms of the compound of formula (I).

In at least one embodiment, the component is an ester of an oxalkylated alkylalkylene diamine of formula (I), wherein
R denotes $C_8$-$C_{18}$-alkyl or $C_8$-$C_{18}$-alkenyl
A denotes a group —$C_2H_4$—
$Z^1$, $Z^2$, $Z^3$ and $Z^4$ are the same and denote —C(O)—R' with
R' being $C_8$-$C_{18}$-alkyl or $C_8$-$C_{18}$-alkenyl
a denotes 0, m denotes 3
u, v and w are each independently numbers from 3 to 9
where the sum of u, v and w being from 6 to 30,
and/or a quaternized salt thereof, where the salt is formed by quaternizing one or two of the nitrogen atoms of the compound of formula (I).

In at least one embodiment, the component is a quaternized salt of an ester of an oxalkylated alkylalkylene diamine of formula (I).

In at least one embodiment, the component is a quaternized salt of an oxalkylated alkylalkylene diamine of formula (I), where the salt is quaternized at one or two of the nitrogen atoms of the compound of formula (I).

In at least one embodiment said component is applied to the hair on a weekly to bi-weekly basis.

Second Aspect

A second aspect relates to the use of a composition for strengthening keratinous fibres or protecting keratinous fibres from damage, wherein the composition comprises a component, wherein the component is an ester of an oxalkylated alkylalkylene diamine of formula (I)

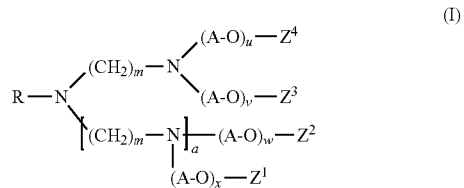

wherein
R denotes $C_8$-$C_{24}$-alkyl or $C_8$-$C_{24}$-alkenyl
A denotes a group —$C_2H_4$— or —$C_3H_6$—, in particular a group —$C_2H_4$—
$Z^1$ denotes a group —C(O)—R', wherein R' denotes $C_5$-$C_{35}$-alkyl or $C_5$-$C_{35}$-alkenyl, in particular $C_8$-$C_{24}$-alkyl or $C_8$-$C_{24}$-alkenyl, $Z^2$ denotes a group —C(O)—R", wherein R" denotes $C_5$-$C_{35}$-alkyl or $C_5$-$C_{35}$-alkenyl, in particular $C_8$-$C_{24}$-alkyl or $C_8$-$C_{24}$-alkenyl, $Z^3$ denotes a group —C(O)—R''', wherein R''' denotes $C_5$-$C_{35}$-alkyl or $C_5$-$C_{35}$-alkenyl, in particular $C_8$-$C_{24}$-alkyl or $C_8$-$C_{24}$-alkenyl, $Z^4$ denotes a group —C(O)—R'''', wherein R'''' denotes $C_5$-$C_{35}$-alkyl or $C_5$-$C_{35}$-alkenyl, in particular $C_8$-$C_{24}$-alkyl or $C_8$-$C_{24}$-alkenyl, a denotes 0 or 1, in particular 0
m denotes 2 or 3, in particular 3
u, v, w and x are each independently numbers from 1 to 9, in particular 2 to 9
where the sum of u, v and w being from 3 to 30, if a=0, and
where the sum of u, v, w and x being from 4 to 35, if a=1,
and/or a quaternized salt thereof.

In at least one embodiment, the composition is a cosmetic composition more preferably a hair conditioning composition.

In at least one embodiment, the composition comprises at least one fatty alcohol having 6 to 18 carbon atoms. The fatty alcohol can serve as lubricant. Optionally a mixture of at least two different fatty alcohols, having 6 to 18 carbon atoms, can be used. Cetearyl alcohol (mixture of cetyl- and stearyl-alcohol) is one useful example.

In at least one embodiment, the component is an ester of an oxalkylated alkylalkylene diamine of formula (I), wherein:
R denotes $C_8$-$C_{24}$-alkyl or $C_8$-$C_{24}$-alkenyl, in particular $C_{10}$-$C_{20}$-alkyl or $C_{10}$-$C_{20}$-alkenyl;
A denotes a group —$C_2H_4$—;
$Z^2$ denotes —C(O)—R", wherein R" denotes $C_8$-$C_{18}$-alkyl or $C_8$-$C_{18}$-alkenyl;
$Z^3$ denotes —C(O)—R''', wherein R''' denotes $C_8$-$C_{18}$-alkyl or $C_8$-$C_{18}$-alkenyl;
$Z^4$ denotes —C(O)—R'''', wherein R'''' denotes $C_8$-$C_{18}$-alkyl or $C_8$-$C_{18}$-alkenyl;
a denotes 0;
m denotes 2 or 3, in particular 3;
u, v and w are each independently numbers from 3 to 9, where the sum of u, v and w being from 6 to 30,
and/or a quaternized salt thereof, where the salt is formed by quaternizing one, two or three, preferably one or two, of the nitrogen atoms of compound of formula (I).

In at least one embodiment, the component is an ester of an oxalkylated alkylalkylene diamine of formula (I), wherein:

R denotes $C_8$-$C_{18}$-alkyl or $C_8$-$C_{18}$-alkenyl;
A denotes a group —$C_2H_4$—;
$Z^2$, $Z^3$ and $Z^4$ are the same and denote —C(O)—R',
and where
R' being $C_8$-$C_{18}$-alkyl or $C_8$-$C_{18}$-alkenyl;
a denotes 0, m denotes 3;
u, v and w are each independently numbers from 3 to 9, where the sum of u, v and w being from 6 to 30;
and/or a quaternized salt thereof, where the salt is formed by quaternizing one or two of the nitrogen atoms of the compound of formula (I).

The numbers u, v and w are often the same numbers, ranging from 5 to 9, often from 5.5 to 7.8. Compounds of formula (I) with n from 7 to 7.8 and $(CH_3SO_4)^-$ as anion are of particular interest.

This cosmetic composition, in particular a hair conditioner, preferably comprises at least one fatty alcohol, preferably having 6 to 18 carbon atoms. In the case of cleansing composition (shampoo) the composition preferably comprises at least one cleansing/foaming agent.

In at least one embodiment, the composition comprises 0.1 wt.-% to 10 wt.-% of the component. In at least one embodiment, the composition comprises 0.5 wt.-% to 8 wt.-%, preferably 0.8 wt.-% to 7 wt.-%, more preferably 1.0 wt.-% to 6 wt.-%, even more preferably 1.2 wt.-% to 5 wt.-%, even more preferably 1.5 wt.-% to 4 wt.-%, most preferably 1.8 wt.-% to 3 wt.-% of the component.

In at least one embodiment said composition is applied to the hair on a weekly to bi-weekly basis.

Further Aspects

The invention also relates to a method of conditioning hair, comprising the steps of applying a conditioning or treatment or mask composition onto wet hair and then removing said conditioner composition from the hair, wherein the composition is according to the second aspect. The conditioner composition according to the second aspect can be used on pre-cleaned hair but also without pre-treatment. In particular, the method relates to treating hair with the intention of repairing hair damage or preventing hair breakage, or strengthening hair, or making hair more resistant to damage, or to withstand further damage.

The invention also relates to a method of treating the hair, comprising the following steps:
    a) applying a shampoo composition onto the hair;
    b) washing the hair with the shampoo composition;
    c) removing the shampoo composition from the hair;
    d) applying a conditioner (or mask or treatment or serum) composition onto wet hair;
    e) rinsing said conditioner (or mask or treatment or serum) composition from the hair,
    wherein the conditioner (or mask or treatment or serum) composition is according to the second aspect.

The described method of treating hair of the present invention may also include one or more additional steps with additional ingredients, such as a color altering composition, a developer composition, a pre-treatment composition and/or a post-treatment composition. Ingredients of the additional steps include well-known conventional additives, typically employed in hair treatment compositions, such as coloring agents, basifying and acidifying agents, buffers, thickening agents, gelling agents, rheology modifiers, antioxidants, fragrances and chelating agents.

The invention also relates to a method of treating the hair, wherein said hair treatment composition comprises a quaternized salt of an oxalkylated alkylalkylene diamine of formula (I), where the salt is quaternized at one or two of the nitrogen atoms of the compound of formula (I). In one embodiment, the hair treatment composition comprises at least one fatty alcohol, having 6 to 18 carbon atoms. In another embodiment, the composition contains at least one cleansing/foaming surfactant.

The invention also relates to a method of treating the hair, wherein said conditioner composition further comprises as lubricant at least one fatty alcohol, having 6 to 18 carbon atoms. Often a mixture of at least two different fatty alcohols, each having 6 to 18 carbon atoms, is used, such as cetearyl alcohol (mixture of cetyl- and stearyl-alcohol).

The invention also relates to a multiple-part kit of hair cleaning and hair conditioning compositions. The term "kit" includes items that are either sold or packaged together. The multiple-part kit may be distributed to end users through salons, but one aspect of the invention involves distributing the kits to consumers through retail sales channels such as drugstores, cosmetic stores and on-line stores. The kit comprises separate compartments with formulations for a shampoo and a conditioning treatment.

The term "compartment" refers to any receptacle, regardless of shape, material or closure, which serves a containing function. The term "compartment" includes the interior of a tube, sack, can, tub, bottle, packet, envelope or other vessel. The components of the multiple-part kit may be contained in a single receptacle, or may be divided amongst multiple receptacles. The multiple-part kit can additionally comprise a compartment with a composition to color the hair and/or a composition to moisturize and maintain the quality of the treated hair.

For bleached or colored hair, additional compartments in the multiple-part kit are advantageous. There is a high need for a hair cleaning and hair conditioning kit, that is easy to use and that provides a consumer specialized care regimen to preserve the condition of the hair. The invention provides all this in one multiple part kit with all the components needed to maintain the condition of the hair for several weeks: The kit may include at least one compartment containing a pretreatment composition. This pre-treatment composition may comprise known natural oils, humectants, non-ionic surfactants, cationic conditioning agents (such as the salts of compounds of formula (I)), plant extracts, vitamins, and organic oils.

DETAILED DESCRIPTION OF ANY FURTHER COMPONENTS

Suitable organic oils include esters of the formula R'CO—OR", wherein R' and R" are each independently a $C_4$-$C_{20}$ straight or branched chain alkyl, alkenyl or alkoxy-carbonylalkyl or alkylcarbonyl-oxyalkyl. Examples of such esters include isotridecyl isononanoate, PEG-4 diheptanoate, isostearyl neopentanoate, tridecyl neopenta-noate, cetyl octanoate, cetyl palmitate, cetyl ricinoleate, cetyl stearate, cetyl myristate, isopropyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol. The organic oil may comprise glyceryl esters of fatty acids, or triglycerides, such as castor oil, lanolin oil, triisocetyl citrate, $C_{10}$-$C_{18}$ triglycerides, caprylic/capric/triglycerides, coconut oil, mineral oil, almond oil, apricot kernel oil, avocado oil, babassu oil, evening primrose oil, camelina sativa seed oil, grape seed oil, macadamia ternifolia seed oil, corn oil, meadowfoam seed oil, mink oil, olive oil, palm kernel oil, safflower oil, sesame oil, soybean oil, sunflower oil, wheat germ oil and *Camellia reticulata* seed oil.

Also suitable as the oils are glyceryl esters (excluding fats and oils which are glyceryl esters of fatty acids) which are primarily fatty acid mono-di- and triglycerides which are modified by reaction with other alcohols, for example, acetylated castor oil, glyceryl stearate, glyceryl dioleate, glyceryl distearate, glyceryl trioctanoate, glyceryl distearate, glyceryllinoleate, glyceryl myristate, glyceryl isostearate, PEG castor oils, PEG glyceryl oleates, PEG glyceryl stearates and PEG glyceryl tallowates.

Also suitable as the organic oil are non-volatile hydrocarbons such as isoparaffins, hydrogenated polyisobutene, mineral oil and squalene. Also suitable as the oil are various lanolin derivatives such as acetylated lanolin, acetylated lanolin alcohol, and various fluorinated oils, such as fluoro guerbet esters or perfluropolyethers. Other suitable oils include sorbitan derivatives such as PEG sorbitan beeswax, PEG sorbitan isostearate, PEG sorbitan lanolate, PEG sorbitan laurate, PEG sorbitan oleate, PEG sorbitan palmitate, PEG sorbitan stearate, polysorbates, sorbitan trioleates, sorbitan sesquioleates, sorbitan stearates, sorbitan tristearates, and so on.

Suitable moisturizers (and humectants) in the compositions include glycerin, propylene glycol, butylene glycol, ethylene glycol, polyethylene glycols, having from 4 to 250 repeating ethylene glycol units, and ethoxy-diglycol. Non-ionic surfactants in the compositions can be alkoxylated derivatives of the following: fatty alcohols, alkyl phenols, fatty acids, fatty acid esters and fatty acid amides, in the $C_{16}$ to $C_{40}$ range, and having from about 1 to about 110 alkoxy groups. The alkoxy groups are selected from the group consisting of $C_2$-$C_6$ oxides and their mixtures, with ethylene oxide, propylene oxide, and their mixtures being the typical alkoxides. The alkyl chain may be linear, branched, saturated, or unsaturated. Of these alkoxylated non-ionic surfactants, the ethoxylated alcohols and propoxylated alcohols are typical. The alkoxylated alcohols may be used alone or in mixtures.

Commercially available, nonionic surfactants are Brij, nonionic surfactants from Uniqema, Willmington. Typically, Brij is the condensation product of aliphatic alcohols with from about 1 to about 54 moles of ethylene oxide, the alkyl chain of the alcohol being typically a linear chain and having from about 8 to about 22 carbon atoms, for example, Brij 72 (i.e., Steareth-2) and Brij 76 (i.e., Steareth-10).

Also useful herein as nonionic surfactants are alkyl glycosides, which are the condensation products of long chain alcohols, e.g. $C_8$-$C_{30}$ alcohols, with sugar or starch polymers. Commercially available examples of these surfactants include decyl polyglucoside (available as APG® 325 CS) and lauryl polyglucoside (available as APG® 6000S and 625 CS), available from Cognis, Ambler.

Other non-ionic surfactants suitable for use in the present invention are glucamides, glyceryl esters and polyglyceryl esters, including glyceryl monesters, typically glyceryl monesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof. Also useful herein as nonionic surfactants are sorbitan esters. Because of the manner in which they are typically manufactured, these sorbitan esters comprise mixtures of mono-, di-, tri-, etc. esters. Representative examples of suitable sorbitan esters include sorbitan monooleate, sorbitan stearates, sorbitan monoisostearate and sorbitan sesquioleate.

For the preparation of the conditioner composition, several cationic components can be used, including cationic quaternary ammonium compounds, amide or amine conditioning agents, and cationic polymers. Suitable classical cationic conditioning agents include cationic quaternary ammonium salts. The aliphatic groups of such quaternary ammonium salts may contain, in addition to carbon atoms, ether linkages as well as amide groups. Suitable quaternary ammonium compounds may be mono-long chain alkyl, di-long chain alkyl, tri-long chain alkyl, and the like. Examples of such quaternary ammonium salts include benzalkonium chloride, benzyl triethyl ammonium chloride, cetyl-triammonium chloride (CTAC), and cetylpyridinium chloride.

Cationic amides are also suitable as further conditioning agents. Also suitable are amidoamine salts, which are the condensation products of fatty acids with polyfunctional amines, for example, those having the formula R'CONH$(CH_2)_n NR_1R_2$ where R'CO is a fatty acyl group such as stearoyl, $R_1$ and $R_2$ are methyl or ethyl, and n is 2 or 3.

Examples of such compounds include stearamido-propyl dimethylamine, see Alzo, Inc. product NECON®. Also suitable are salts of fatty primary, secondary, or tertiary amines, wherein the substituted groups have 12 to 22 carbon atoms. Examples of such amines include dimethyl stearamine, dimethyl soyamine, stearylamine, myristylamine, tridecylamine and -ethyl stearamine.

As cationic components, a variety of cationic polymers are suitable, including quaternized cellulose ethers, copolymers of vinylpyrrolidone, acrylic polymers, including homopolymers or copolymers of dimethyldiallylammonium chloride and acrylamide. Such compounds are sold under MERQUAT® (Merck). Also suitable are various types of homo- or copolymers derived from acrylic or methacrylic acid, acrylamide, methylacrylamide, diacetone-acrylamide.

For the method of treating hair according to the invention, a shampoo composition can be used, but the conditioner (mask, treatment, serum) composition can also be used without using a shampoo composition. The shampoo compositions are generally comprised of from 1 to 99%, preferably from 5 to 95%, more preferably from 10 to 90% by weight of the total composition of water, and from 0.1 to 99%, preferably from 1 to 95%, more preferably from 5 to 90% by weight of the total composition of a cleansing surfactant. Suitable cleansing surfactants are generally anionic, amphoteric, betaine, or zwitterionic surfactants. Preferably, anionic surfactants include alkyl ether or alkyl ether sulfates such as sodium laureth-sulfate, sodium lauryl sulfate, and other components described above.

The conditioner compositions of the invention generally comprise from 0.1 to 99%, preferably from 0.5 to 95%, more preferably from 1 to 90% by weight, of the total conditioner composition, of water and from 0.1 to 99%, preferably from 0.5 to 95%, more preferably from 1 to 90% by weight of the total conditioner composition of one or more further components. These further components comprise at least one ester of an oxalkylated alkylalkylene diamine of formula (I), and/or a quaternized salt thereof.

The conditioner composition of the invention generally comprises from 0.1 to 10%, preferably from 0.2 to 9%, more preferably from 0.5 to 8% by weight of the total conditioner composition, of at least one ester of an oxalkylated alkylalkylene diamine of formula (I) and/or a quaternized salt thereof.

In one embodiment, the hair conditioner composition comprises 0.5 to 10% by weight, often 0.7 to 8% by weight, of at least one fatty alcohol component, having 6 to 22 carbon atoms. Often, a mixture of at least two fatty alcohol components is used with a total amount of 0.5 to 10% by weight, often 0.7 to 8% by weight.

In one embodiment, the hair conditioner composition comprises 0.5 to 8% by weight of at least one ester of an oxalkylated alkylalkylene diamine of formula (I) and/or a quaternized salt thereof and 0.7 to 8% by weight of a mixture of at least two fatty alcohol components, each having 6 to 22 carbon atoms.

The conditioner composition of the invention, in addition to water and the oxalkylated alkylalkylene diamine of formula (I) and/or the quaternized salt thereof, often comprises one or more of the following further components: acidity regulators, antistatic agents, glossers, lubricants, moisturizers, oils, preservatives, sequestrants, strengtheners, sun protectors, further surfactants (such as cetyl trimethylammonium chloride, CTAC) and thermal protectors.

Typical glossers are silicones. Suitable as silicones are volatile or nonvolatile non ionic silicone fluids, silicone resins, and silicone semisolids or solids. Volatile silicones are linear or cyclic silicones having a measureable vapor pressure, which is defined as a vapor pressure of at least 2 mm of mercury at 20° C. Also suitable are water insoluble nonvolatile silicone fluids including polyalkyl siloxanes, polyaryl siloxanes, polyalkylaryl siloxanes, polyether siloxane copolymers, amine-functional silicones, and mixtures thereof.

Typical oils are organic oils, which often are esters of the formula R'CO—OR" presented above. The organic oil component may also comprise glyceryl esters of fatty acids, or triglycerides, coconut oil, almond oil, apricot kernel oil, avocado oil, babassu oil, evening primrose oil, camelina sativa seed oil, grape seed oil, macadamia ternifolia seed oil, corn oil, meadowfoam seed oil, mink oil, olive oil, palm kernel oil, safflower oil, sesame oil, soybean oil, sunflower oil, wheat germ oil, and *Camellia reticulata* seed oil. Also suitable as the oil component are sorbitan esters and glyceryl esters as described above.

The conditioning composition may also contain further surfactants (not according to formula I), such as those mentioned above. The conditioning composition of the invention often contains at least 0.1% by weight, preferably from 0.1 to 10% by weight, preferably from 0.2 to 5% by weight (of the total composition), of at least one further surfactant, in particular of CTAC.

The conditioning composition of the invention often contains at least about 0.5% by weight, preferably from 0.5 to 10% by weight, often from 0.7 to 8% by weight (of the total composition), of at least one lubricant, in particular a fatty alcohol component, preferably having 6 to 22 carbon atoms. Often, a mixture of at least two fatty alcohol components (e.g. cetyl alcohol and stearyl alcohol with 50:50% by weight) is used with a total amount of 0.5 to 10% by weight, often 0.7 to 8% by weight.

The conditioning composition of the invention often contains at least 0.05% by weight, often from 0.05 to 5% by weight (of the total composition), of at least one oil component. In one embodiment, the conditioning composition contains at least 0.5% by weight, often from 0.5 to 5% by weight (of the total composition) of at least one oil component.

The conditioning composition of the invention can contain from 0.1 to 10% by weight, often from 0.1 to 5%, in particular from 0.5 to 5% by weight (of the total composition), of at least one polymer component (having a molecular weight from 50.000 to 5.000.000 g/mol) from the group of: polyamines, polyaminoamides or poly (quaternary ammonium) polymers, (such as vinylpyrrolidone/dialkylaminoalkyl acrylate or methacrylate copolymers), or carbomer products (such as Carbopol 980), cellulose ether derivatives containing quaternary ammonium groups, cationic cellulose derivatives such as cellulose copolymers or cellulose derivatives grafted with a water-soluble quaternary ammonium monomer quaternized polysaccharides homopolymer of dimethyldiallylammonium chloride (such as MERCK products MERQUAT© 100 or MERQUAT® 550), quaternary polymers of vinylpyrrolidone and of vinylimidazole, cationic polysiloxanes such as described in U.S. Pat. No. 4,185,087, poly (quaternary ammonium) polymers.

In at least one embodiment, the composition comprises at least one rheology modifying agent, preferably a gelling and/or thickening agent. The conditioning composition of the invention can contain from 0.1 to 10% by weight, often from 0.2 to 5% by weight, in particular 0.5 to 5% by weight (of the total composition), of at least one rheology modifying agent, in particular gelling and thickening agent. Examples are cellulosic thickeners, for example, hydroxyethyl-cellulose, hydroxypropylcellulose, and carboxymethylcellulose, guar gum, such as hydroxypropylguar, gums of microbial origin, such as xanthan gum and scleroglucan gum, and synthetic thickeners, such as crosslinked homo- or copolymers of acrylic acid and/or of acrylamidopropanesulphonic acid. Other rheology modifying agents include fatty acid amides such as coconut diethanolamide and monoethanolamide, and oxyethylenated monoethanolamide of carboxylic acid alkyl ether.

In the method of the invention the conditioner composition is applied to the (wet) hair. Before the conditioner composition is applied, according to one embodiment, a shampoo composition can be applied to the hair for a period of time ranging from about 30 seconds to 5 minutes. The shampoo composition is then rinsed from the hair using water.

The conditioner composition comprising the esters of an oxalkylated alkylalkylene diamines of formula (I) and/or a quaternized salts thereof (and often the lubricant), is combined with water and the mixture is then applied to the hair.

The mixture may be left on the hair for about 1 to 10 minutes, or rinsed immediately, or as recommended in the instructions given in the product or kit. After the indicated amount of time has elapsed, the mixture is rinsed off the hair with water. Finally, a post-treatment composition can be applied to the hair and may or may not be rinsed off. Following the application of the post-treatment composition, the hair can be brought to the style as desired.

The shampoo composition and/or the conditioner composition, and/or the post-treatment composition can be provided in a kit such that they may be used on a daily, bi-weekly or weekly basis, depending on the needs of the consumer. Preferably, the shampoo and conditioner compositions are used on a weekly to bi-weekly basis.

EXAMPLES

The examples which follow are intended to illustrate the subject matter of the invention without restricting it thereto.

Example 1: Synthesis of Conditioning Materials

The following compounds (mixtures) were synthesized:

Compound A

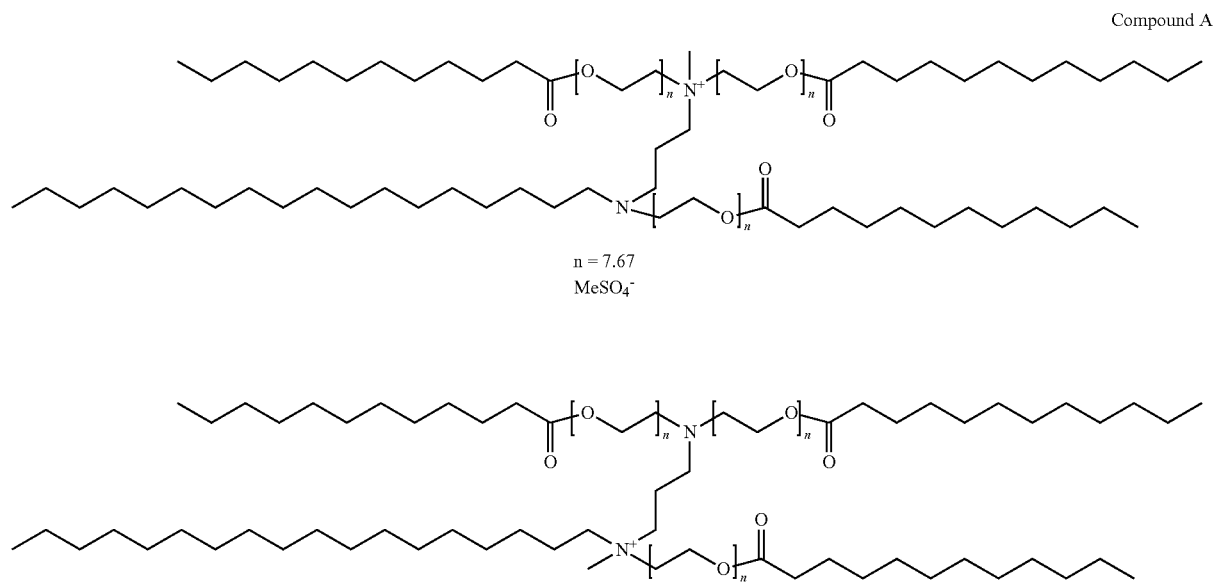

n = 7.67
MeSO$_4^-$ 203.7 g (0.1 mol) of a compound with the formula (I) with R=C-Chain derived from tallow fatty acid (C$_{16}$/C$_{18}$), a=0, m=3, A=—C$_2$H$_4$—, u+v+w=23, Z$^2$=Z$^3$=Z$^4$=C-chain derived from cocos fatty acid (C$_{12}$/C$_{14}$) were initially charged in a 1 L flask equipped with a reflux condenser and a thermometer and heated to 60° C. While stirring, 12.3 g (0.1 mol) dimethyl sulfate were added dropwise within 30 minutes. During that period, the temperature raised to 80° C. The reaction mixture was stirred for 5 h at 80° C. After cooling to room temperature, 207.6 g product were obtained (Bas.N=0.67%) as transparent yellow-brown liquid.

The same procedure is used as above except that cocos fatty acid is used.

Example 2: Preparation of Hair Care Products 2.1. Benchmark Conditioner:

| Ingredient, INCI name | Active level, % |
|---|---|
| Cetearyl alcohol | 4 |
| Behentrimonium chloride | 2 |
| Water | Add to 100% |

Compound B

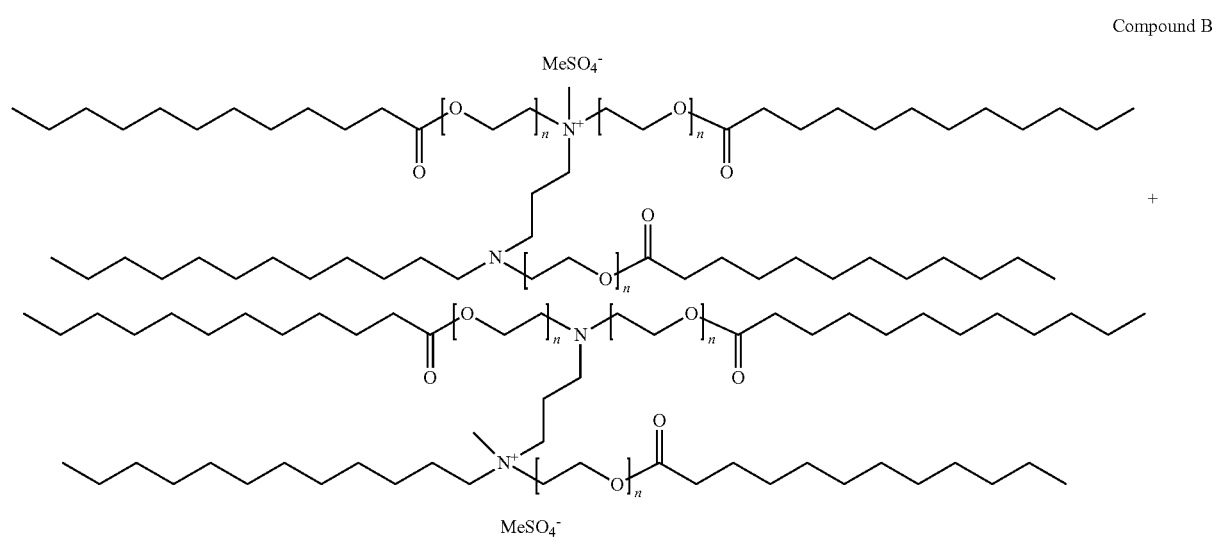

n = 7.67

2.2. Hair Repair Conditioner:

| Ingredient, INCI name | Active level, % |
| --- | --- |
| Cetearyl alcohol | 4 |
| Compound B | 2 |
| Water | Add to 100% |

2.3. Transparent-Hair-Repair-Conditioner

| Ingredient, INCI name | Active level, % |
| --- | --- |
| Aqua | To 100 |
| Glycerin | 5.00 |
| PEG-7 Glyceryl Cocoate | 3.00 |
| Compound A | 2.00 |
| PEG-40 Hydrogenated Castor Oil | 2.00 |
| Hydroxyethylcellulose | 1.25 |
| Phenoxyethanol (and) Benzoic Acid (and) Piroctone Olamine | 1.20 |
| Fragrance | 0.60 |
| Glycerin, Aqua, Hibiscus Sabdariffa Flower Extract | 0.50 |
| Glycerin, Aqua, Euterpe Oleracea Fruit Extract | 0.50 |
| Gossypium Herbaceum (Cotton) Seed Oil | 0.50 |
| Disodium EDTA | 0.10 |
| Benzophenone-4 | 0.05 |
| Dye | q.s. |

2.4. Transparent Hair Repair Shampoo

| Ingredient, INCI name | Active level, % |
| --- | --- |
| Aqua | To 100 |
| Glycerin | 5.00 |
| PEG-7 Glyceryl Cocoate | 3.00 |
| Compound A | 2.00 |
| PEG-40 Hydrogenated Castor Oil | 2.00 |
| Hydroxyethylcellulose | 1.25 |
| Phenoxyethanol (and) Benzoic Acid (and) Piroctone Olamine | 1.20 |
| Fragrance | 0.60 |
| Glycerin, Aqua, Hibiscus Sabdariffa Flower Extract | 0.50 |
| Glycerin, Aqua, Euterpe Oleracea Fruit Extract | 0.50 |
| Gossypium Herbaceum (Cotton) Seed Oil | 0.50 |
| Disodium EDTA | 0.10 |
| Benzophenone-4 | 0.05 |
| Dye | q.s. |

Example 3: Hair Tests Using Formulation 2.2. and 2.1. (Benchmark)

Hair swatches from Kerling, Germany were used for evaluation. In particular, we used Caucasian hair, damaged (bleached for 4 h). Hair swatches were pre-washed two times with a 14% solution of sodium laureth sulfate in water, rinsed, and the conditioner was applied. After massaging and rinsing off the conditioner, swatches were dried for 12 h in air, in the environment of controlled humidity (40%) and temperature (22° C.).

Hair tests were performed using a multiple hair combing device: a rotating cylinder comprising six combs. Three hair switches are treated with a product, dried, and mounted simultaneously on the device. They were next combed at a defined rate (50 rpm/min) for a period of time (2-10 h). The broken hairs that fell down were counted. The hair product which leads to fewer broken hairs has the repair/damage prevention/damage protection/hair strengthening properties. Number of broken hairs, from image analysis using ImageJ software (https://imagej.nih.gov/ij/)

| Formulation | Number of broken hairs after hours of combing: | | | | |
| --- | --- | --- | --- | --- | --- |
| | 2 h | 4 h | 6 h | 8 h | 10 h |
| 2.1. | 9 | 25 | 57 | 112 | 118 |
| 2.2 | 7 | 11 | 14 | 16 | 16 |

From the results above it is clear that using the conditioner containing Compound B has a very strong hair repairing effect in comparison to behentrimonium chloride. Behentrimonium chloride is at present the key component used in cosmetic hair products intended for hair repair/damage prevention/prevention of breakage/hair strengthening.

In particular, the Mintel database (accessed 6 Feb. 2018) shows that behentrimonium chloride is included in 45.4% of all hair conditioners intended (claimed) for damaged hair globally. Cetearyl alcohol is present in 69.9% of products.

The invention claimed is:

1. A method for strengthening hair or protecting hair from damage, comprising the step of contacting the hair with a composition comprising 0.1 to 10 wt.-% of a component which is an ester of an oxalkylated alkylalkylene diamine of formula (I)

$$R-N\begin{pmatrix}(CH_2)_m-N\begin{pmatrix}(A-O)_u-Z^4\\(A-O)_v-Z^3\end{pmatrix}\\[(CH_2)_m-N]_a-(A-O)_w-Z^2\\(A-O)_x-Z^1\end{pmatrix} \quad (I)$$

wherein
R is $C_5$-$C_{24}$-alkyl or $C_8$-$C_{24}$-alkenyl
A is a group —$C_2H_4$— or —$C_3H_6$—,
$Z^1$ is a group —C(O)—R', wherein R' is $C_5$-$C_{35}$-alkyl or $C_5$-$C_{35}$-alkenyl,
$Z^2$ is a group —C(O)—R", wherein R" is $C_5$-$C_{35}$-alkyl or $C_5$-$C_{35}$-alkenyl,
$Z^3$ is a group —C(O)—R''', wherein R''' is $C_5$-$C_{35}$-alkyl or $C_5$-$C_{35}$-alkenyl,
$Z^4$ is a group —C(O)—R"", wherein R"" is $C_5$-$C_{35}$-alkyl or $C_5$-$C_{35}$-alkenyl,
a is 0 or 1,
m is 2 or 3,
u, v, w and x are each independently numbers from 1 to 9,
where the sum of u, v and w being from 3 to 30, if a=0, and
where the sum of u, v, w and x being from 4 to 35, if a=1, and/or a quaternized salt thereof.

2. The method according to claim 1, wherein the component is an ester of an oxalkylated alkylalkylene diamine of formula (I), wherein
R is $C_5$-$C_{24}$-alkyl or $C_5$-$C_{24}$-alkenyl
A is a group —$C_2H_4$—
$Z^1$ is —C(O)—R', wherein R' is $C_8$-$C_{18}$-alkyl or $C_8$-$C_{18}$-alkenyl
$Z^2$ is —C(O)—R", wherein R" is $C_8$-$C_{18}$-alkyl or $C_8$-$C_{18}$-alkenyl $Z^3$ is —C(O)—R′″, wherein R′″ is $C_8$-$C_{18}$-alkyl or $C_8$-$C_{18}$-alkenyl $Z^4$ is —C(O)—R″″, wherein R″″ is $C_8$-$C_{18}$-alkyl or $C_8$-$C_{18}$-alkenyl a is 0 m is 2 or 3, u, v and w are each independently numbers from 3 to 9 where the sum of u, v and w being from 6 to 30, and/or a quaternized salt thereof, where the salt is formed by quaternizing one or two of the nitrogen atoms of the compound of formula (I).

3. The method according to claim 1, wherein the component is an ester of an oxalkylated alkylalkylene diamine of formula (I), wherein R is $C_8$-$C_{18}$-alkyl or $C_8$-$C_{18}$-alkenyl A is a group —$C_2H_4$-

$Z^1$, $Z^2$, $Z^3$ and $Z^4$ are the same a is 0 m is 3 u, v and w are each independently numbers from 3 to 9 where the sum of u, v and w being from 6 to 30, and/or a quaternized salt thereof, where the salt is formed by quaternizing one or two of the nitrogen atoms of the compound of formula (I).

4. The method according to claim 1, wherein the component is a quaternized salt of an ester of an oxalkylated alkylalkylene diamine of formula (I).

5. The method according to claim 1, wherein the composition further comprises water and 0.5 to 10 wt.-% of at least one fatty alcohol compound, having 6 to 18 carbon atoms.

6. The method according to claim 1, wherein the composition further comprises at least one acidity regulator, at least one glosser, and at least one surfactant.

7. The method according to claim 1, wherein the composition further comprises a surfactant selected from the group consisting of non-polymeric, cationic quaternary ammonium surfactants.

8. The method according to claim 7, wherein the surfactant is cetyl trimethylammonium chloride.

9. The method according to claim 1, wherein the composition further comprises at least one rheology modifying agent.

10. The method according to claim 1, wherein the component is a quaternized salt of an oxalkylated alkylalkylene diamine of formula (I), where the salt is quaternized at one or two of the nitrogen atoms of the compound of formula (I).

11. The method according to claim 1, wherein the composition is applied to the hair on a weekly to bi-weekly basis.

12. The method according to claim 1, wherein

A is —$C_2H_4$—

R' is $C_8$-$C_{24}$-alkyl or $C_8$-$C_{24}$-alkenyl,

R" is $C_8$-$C_{24}$-alkyl or $C_8$-$C_{24}$-alkenyl,

R′″ is $C_8$-$C_{24}$-alkyl or $C_8$-$C_{24}$-alkenyl,

R″″ is $C_8$-$C_{24}$-alkyl or $C_8$-$C_{24}$-alkenyl,

A is 0, m is 3.

* * * * *